(12) United States Patent
Greenbaum et al.

(10) Patent No.: US 6,569,384 B2
(45) Date of Patent: May 27, 2003

(54) TISSUE-BASED WATER QUALITY BIOSENSORS FOR DETECTING CHEMICAL WARFARE AGENTS

(75) Inventors: Elias Greenbaum, Oak Ridge, TN (US); Charlene A. Sanders, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 171 days.

(21) Appl. No.: 09/773,641

(22) Filed: Jan. 31, 2001

(65) Prior Publication Data

US 2002/0102629 A1 Aug. 1, 2002

Related U.S. Application Data (60) Provisional application No. 60/226,646, filed on Aug. 21, 2000.

(51) Int. Cl.$^7$ ............................................. G01N 15/06
(52) U.S. Cl. .................................. 422/68.1; 422/82.08
(58) Field of Search ............................ 422/68.1, 82.08

(56) References Cited

U.S. PATENT DOCUMENTS

| | | | |
|---|---|---|---|
| 4,500,641 A | | 2/1985 | van den Engh et al. |
| H454 H | | 4/1988 | Sickenberger et al. .......... 73/27 |
| 4,752,226 A | | 6/1988 | Akers et al. .................. 434/11 |
| 4,906,440 A | | 3/1990 | Kolesar ....................... 422/98 |
| 4,942,303 A | * | 7/1990 | Kolber et al. ............. 250/458.1 |
| H1344 H | | 8/1994 | Baldauf ....................... 435/20 |
| 5,866,430 A | | 2/1999 | Grow ......................... 436/172 |
| 5,874,046 A | * | 2/1999 | Megerle ..................... 422/68.1 |
| 5,922,183 A | | 7/1999 | Rauh ......................... 204/403 |
| 5,965,882 A | | 10/1999 | Megerle et al. ............. 250/287 |
| 6,121,053 A | | 9/2000 | Kolber et al. |
| 6,187,530 B1 | * | 2/2001 | Scholin et al. ................. 435/4 |

FOREIGN PATENT DOCUMENTS

| | | |
|---|---|---|
| DD | 248433 A1 | 8/1987 |
| DE | 19857792 A1 | 7/2000 |
| EP | 0811842 A1 | 12/1997 |
| WO | WO 99/32876 | 7/1999 |

OTHER PUBLICATIONS

Krause, G. H. and Weis, E., (1991) Chlorophyll fluorescence and photosynthesis: the basics, *Annu. Rev. Plant Physiol. Plant Mol. Biol.* 42:313–349.

Krause, G. H., Vernotte, C., and Briantais, J.–M., (1982) Photoinduced quenching of chlorophyll fluorescnence in intact chloroplasts and algae. *Biochimica et Biophysica Acta*. 679: 116–124.

Schreiber, U., Biler, W., and Neubauer, C., (1994) Chlorophyll fluorescence as a nonintrusive indicator for rapid assessment of in vivo photosynthesis. *Ecological Studies* 100: 49–70.

Genty, B., Briantais, J.–M., and Baker, N. R., (1989) The relationship between the quantum yield of photosynthetic electron transport and quenching of chlorophyll fluorescence. *Biochimica et Biophysica Acta*. 990:87–92.

Van Kooten O. and Snel J. F.H. (1990) the use of chlorophyll fluorescence nomenclature in plant stress physiology. Photosynsthesis Research 25:147–150.

Edwards, G. E. and Baker, N. R., (1993) Can $CO_2$ assimilation in maize leaves by predicted accurately from chlorophyll fluorescence analysis? *Photo. Res.* 37: 89–102.

Seaton, G. G. R. and Walker, D. A., (1995) Chlorophyll fluorescence as a measure of photosynthetic carbon assimilation. *Proc. R. Soc. London Ser. B.* 242: 99–108.

Naessens, M., Leclerc J.C., Tran–Minh, C. 2000. Fiber optic biosensor using *Chlorella vulgaris* for determination of toxic compounds. Ecotoxicol. Environ. Saf., 46, 181–185.

Internet Web Site http://www.walz.com e.g., http://www.walz.com/xepam.htm and http://www.walz.com/pamzta.htm.

\* cited by examiner

*Primary Examiner*—Ralph Gitomer
*Assistant Examiner*—Lynda T Guo
(74) *Attorney, Agent, or Firm*—Joseph A. Marasco

(57) ABSTRACT

A water quality sensor for detecting the presence of at least one chemical or biological warfare agent includes: a cell; apparatus for introducing water into the cell and discharging water from the cell adapted for analyzing photosynthetic activity of naturally occurring, free-living, indigenous photosynthetic organisms in water; a fluorometer for measuring photosynthetic activity of naturally occurring, free-living, indigenous photosynthetic organisms drawn into the cell; and an electronics package that analyzes raw data from the fluorometer and emits a signal indicating the presence of at least one chemical or biological warfare agent in the water.

2 Claims, 6 Drawing Sheets

TISSUE-BASED WATER QUALITY BIOSENSORS FOR DETECTING CHEMICAL WARFARE AGENTS

CROSS-REFERENCE TO RELATED APPLICATION

This application claims the benefit of U.S. Provisional Application No. 60/226,646, filed on Aug. 21, 2000, the entire disclosure of which is incorporated herein by reference.

The United States Government has rights in this invention pursuant to contract no. DEAC05-00OR22725 between the United States Department of Energy and UT-Battelle, LLC.

FIELD OF THE INVENTION

The present invention relates to tissue-based sensors for detecting chemical and/or biological contaminants in water, and more particularly to sensors based on changes of quantum yield of fluorescence in which indigenous photosynthetic tissues that are naturally present in water are used as a sensor materials for detecting chemical and/or biological warfare agents in the water.

BACKGROUND OF THE INVENTION

Various sensors have been used to monitor water quality. Currently available water quality sensor technology is based generally on adaptations, modifications, and extensions of conventional analytical chemistry equipment and techniques. Some examples follow.

U.S. Pat. No. 5,965,882 issued on Oct. 12, 1999 to Megerle et al. describes a miniaturized ion mobility spectrometer sensor cell that comprised an improved spectrometer for detecting chemical warfare agents and hazardous vapors.

U.S. Pat. No. 5,922,183 issued on Jul. 13, 1999 to Rauh describes a metal oxide matrix. Thin film composites of the oxides and biological molecules such as enzymes, antibodies, antigens and DNA strands can be used for both amperometric and potentiometric sensing.

U.S. Pat. No. 5,866,430 issued on Feb. 2, 1999 to Grow describes a methodology and devices for detecting or monitoring or identifying chemical or microbial analytes. The described methodology comprises four basic steps: (1) The gas or liquid medium to be monitored or analyzed is brought into contact with a bioconcentrator which is used to bind with or collect and concentrate one or more analytes. (2) The bioconcentrator-analyte complex is then exposed to radiation of one or more predetermined wavelengths to produce Raman scattering spectral bands. (3) At least a portion of the Raman spectral bands is collected and processed by a Raman spectrometer to convert the same into an electrical signal. And (4) the electrical signal is processed to detect and identify, qualitatively and/or quantitatively, the analyte(s).

U.S. SIR No. H1344 issued on Aug. 2, 1994 to Baldauf et al describes a portable automatic sensor for toxic gases. Their method provided for the integration of a low-volume liquid flow and sampling system and a portable optical waveguide-based fluorescence detector for the chemical analysis of reagents in fluorescence-based reactions. In a preferred embodiment, the presence and concentration of acetylcholinesterase inhibitors, such as chemical warfare nerve agents or certain insecticides, is determined by mixing aqueous samples with a dilute solution of n-methyl indoxyl acetate, and monitoring the formation of a fluorescent product (n-methyl indoxyl).

U.S. Pat. No. 4,906,440 issued on Mar. 6, 1990 to Kolesar describes a sensor for detecting chemicals. In this sensor a gas detector is described that detects the presences of the gas when the gas reacts with a distributed RC notch network to cause a shift in operating frequency and notch depth. A metallic/metallic oxide gas sensitive discontinuous film acts as the distributive resistive element in the RC notch network. The gas changes the conductivity of the film and this causes the network to react. In the preferred embodiment, a copper/cuprous oxide film detects organophosphorus compounds, which can be chemical warfare agents.

U.S. Pat. No. 4,752,226 issued on Jun. 21, 1988 to Akers et al. describes a method for simulating chemical warfare attack that includes the use of a radiant energy transmitting device for radiating energy in a pattern which simulates different types and forms of chemical agents. Protective devices, such as gas masks, protective clothing, or structures, are provided with sensors for determining whether the protective device is properly employed.

U.S. SIR No. H454 issued on Apr. 5, 1988 to Sickenberger, et al. describes a method of detecting leaks within artillery shells, bombs and other munitions which involves the permanent in situ insertion within the munitions cavity of an electrically resistive surface which varies in resistance with the adsorption of leaking chemical vapors. In a typical embodiment of the invention, the electrically resistive surface is serially connected with an identical surface with an inert coating and the voltage drops across both the coated and uncoated surfaces are measured.

It is well-known that there is a close correlation between photosynthetic activity and fluorescence from plants. The following scientific and technical publications are recommended for a basic understanding of the technology:
1. Krause, G. H. and Weis, E., (1991) Chlorophyll fluorescence and photosynthesis: the basics, *Annu. Rev. Plant Physiol. PlantMol. Biol.* 42: 313–349.
2. Krause, G. H., Vernotte, C., and Briantais, J.-M., (1982) Photoinduced quenching of chlorophyll fluorescence in intact chloroplasts and algae. *Biochimica et Biophysica Acta.* 679:116–124.
3. Schreiber, U., Bilger, W., and Neubauer, C., (1994) Chlorophyll fluorescence as a nonintrusive indicator for rapid assessment of in vivo photosynthesis. *Ecological Studies* 100: 49–70.
4. Genty, B., Briantais, J.-M., and Baker, N. R., (1989) The relationship between the quantum yield of photosynthetic electron transport and quenching of chlorophyll fluorescence. *Biochimica et Biophysica Acta.* 990:87–92.
5. Van Kooten and Snel (1990) tabulated the use of chlorophyll fluorescence nomenclature in plant stress physiology. ??
6. Edwards, G. E. and Baker, N. R., (1993) Can $CO_2$ assimilation in maize leaves by predicted accurately from chlorophyll fluorescence analysis? *Photo. Res.* 37: 89–102.
7. Seaton, G. G. R. and Walker, D. A., (1995) Chlorophyll fluorescence as a measure of photosynthetic carbon assimilation. *Proc. R. Soc. London Ser. B.* 242: 99–108.
8. Naessens, M., Leclerc J. C., Tran-Minh, C. 2000. Fiber optic bio sensor using *Chlorella vulgaris* for determination of toxic compounds. Ecotoxicol. Environ. Saf, 46, 181–185.

Naessens et al. have reported a fiber optic biosensor using entrapped *Chlorella vulgaris* for determination of toxic compounds in water. Naessens et al. uses filter paper-entrapped Chlorella and flows a water sample through the filter-paper. The entrapped algae are an integral part of the instrument. A disadvantage of a system using entrapped algae is that fouling of the sensor is a serious problem since the instrument is useless after such fouling until a new sensor is installed. This is not practical for remote, continuous monitoring.

A treatise on chemical warfare agents may also be helpful. See, for example, Satu M. Sonami, *Chemical Warfare Agents* Academic Press, 1992.

OBJECTS OF THE INVENTION

Accordingly, objects of the present invention include: an indigenous-photosynthetic-tissue-based biosensor for detecting chemical and biological warfare agents wherein the sensing principle is based on changes in the fluorescence induction curve and the overall quantum yield of fluorescence; a means for measuring water quality; a means for detecting contaminants in water; a tissue-based water quality sensor which utilizes indigenous organisms naturally present in water as biosensor materials for detecting chemical and biological warfare agents; a tissue-based water quality sensor wherein the sensor material is not integral with the sensor instrument; and a tissue-based water quality sensor wherein the sensor material is continuously renewed by flowing water. Further and other objects of the present invention will become apparent from the description contained herein.

SUMMARY OF THE INVENTION

In accordance with one aspect of the present invention, the foregoing and other objects are achieved by a tissue-based water quality sensor for detecting the presence of at least one chemical or biological warfare agent including: a cell; means for introducing water into the cell and discharging water from the cell adapted for analyzing photosynthetic activity of naturally occurring, free-living, indigenous photosynthetic organisms in water; a fluorometer having sufficient sensitivity for measuring photosynthetic activity of naturally occurring, free-living, indigenous photosynthetic organisms drawn into the cell; and transmitting means for transmitting analytical data relating to the presence of at least one chemical or biological warfare agent in the water.

In accordance with another aspect of the present invention, a method of testing water to detect the presence of at least one chemical or biological warfare agent includes the steps of:

a. exposing water to a measuring means for measuring photosynthetic activity of free-living indigenous photosynthetic organisms;

b. measuring photosynthetic activity of free-living indigenous photosynthetic organisms occurring naturally in the water to detect the presence of at least one chemical or biological warfare agent in the water.

For a better understanding of the present invention, together with other and further objects, advantages and capabilities thereof, reference is prepared to the following disclosure and appended claims in connection with the above-described drawings.

DETAILED DESCRIPTION OF THE INVENTION

This invention is in the field of tissue-based biosensors. More particularly it utilizes photosynthetic microorganisms such as green algae and cyanobacteria for the detection of chemical warfare agents in drinking water sources. The principle of operation of the detector is based on the well-known scientific fact that the quantum yield of fluorescence is dependent on the ability of photosynthetic organisms to perform photosynthesis. This phenomenon is used in the present invention to construct biosensors that can be used for the rapid detection of, for example, chemical warfare agents in the field. All natural sources of water that are exposed to sunlight contain such algae. Water from a selected source is drawn into a cell and the fluorescence monitored with a compact optoelectronic recording system. Combined with a cell modem and encrypted communications, it is possible, for example to send coded messages to field commanders informing them of the safety of drinking water supplies in a war zone.

As water samples are passed through the cell, any component of the water that negatively impacts photosynthetic capability will cause a change in the fluorescence induction curve, with resultant changes in the quantum yield of fluorescence. As described in further detail below, the change in fluorescence represents a decrease in photosynthetic capability. Different chemical warfare agents will have different influences on the photosynthetic apparatus of a particular alga or cyanobacterium. And the same chemical agent will affect the fluorescence of different organisms in different ways. Some will cause an increase, while others will cause a decrease in fluorescence (non-photochemical quenching of fluorescence). Specific antagonists combined with specific algae or cyanobacteria will cause characteristic changes that can be used to construct a look-up library or database of cause and effect combinations.

Water-soluble toxic chemical and/or biological agents, for example, blood agents, cyanide, pesticides (methyl parathion, for example) and herbicides (DCMU, for example) could pose a threat to potable drinking water supplies. Every water source that is exposed to sunlight contains populations of photosynthetic microorganisms (phytoplankton and algae, for example), at concentrations ranging from 10 to as high as 100,000 organisms/ml. Although always present in sunlight-exposed water, these microorganisms are often invisible to the unaided eye. Phytoplankton emits a characteristic fluorescence signal that, if detectable in solutions with low microorganism concentrations, can be utilized as an in situ indicator of chemical and/or biological warfare agents in the water supply. Pesticides, herbicides and cyanide have been detected in "as is" algal liquid cultures, solely by measuring alterations in algal fluorescence emissions.

Algae in water at concentrations found in natural aquatic environments were tested for feasibility as biosensors for water-soluble herbicides, pesticides and cyanide.

EXAMPLE I

Figure 1:
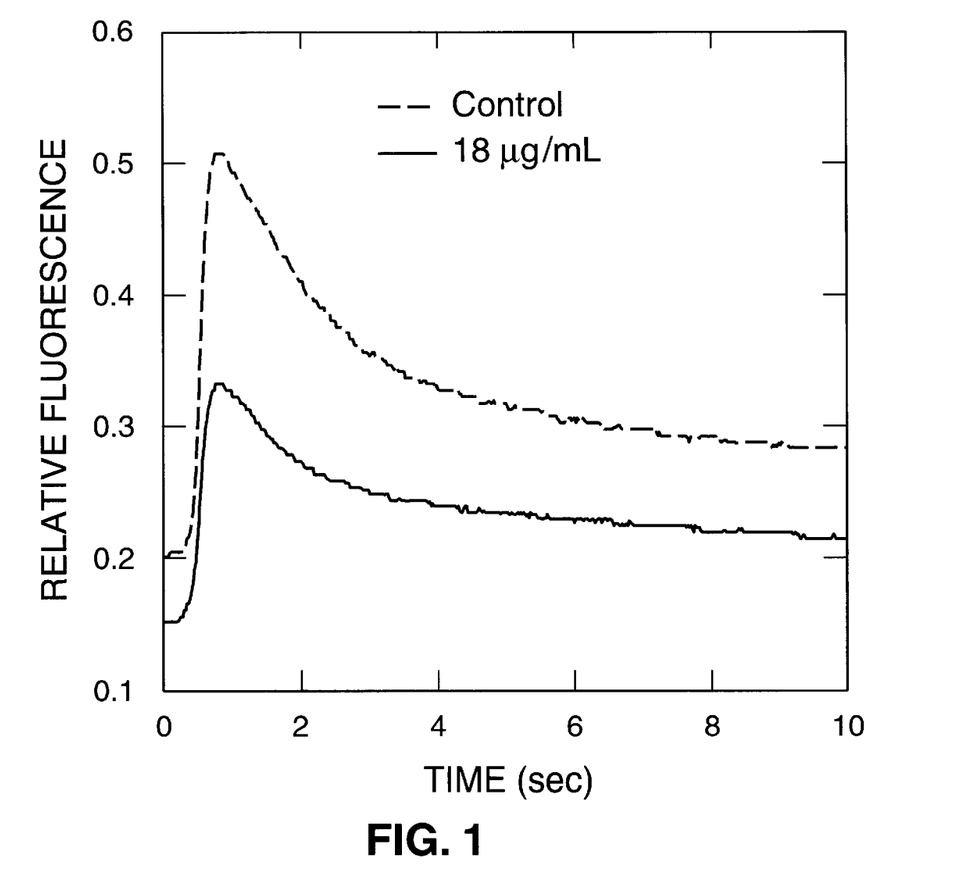
FIG. 1. is a graph illustrating fluorescence induction curves from plankton in water taken from the Clinch river, Oak Ridge, Tenn. in the presence and absence of methyl parathion.

FIG. 1 is an illustration of the detection of methyl parathion, a commercially available insecticide and cholinesterase inhibitor. The water sample was taken directly from the Clinch River, Oak Ridge, Tenn. and analyzed "as is." A Walz XE-PAM pulse-amplitude-modulation fluorometer was used to monitor fluorescence emitted from the naturally occurring algae in the river water. The sample was placed in a cuvette (3 ml) in the fluorometer optical compartment. An actinic light pulse (500 $\mu$E/m$^2$/sec) from the fluorometer's halogen lamp illuminated the sample for 10 seconds and fluorescence induction curves were recorded. Eight minutes after the initial measurement (control period), methyl parathion was added to the sample to a final concentration of 18 $\mu$g/mL. The control fluorescence induction curve and the curve after exposure to the methyl parathion are presented in FIG. 1. A clear change in the initial fluorescence ($F_o$) and maximum fluorescence ($F_{max}$) can be observed in the figure. Moreover, the distinction between control and methyl parathion-treated sample persists over the entire time course of the 10-second measurement. This fluorometric sensing technique can be used to detect the presence of methyl parathion in algae-containing primary drinking water sources.

A useful number that may be derived from the fluorescence curves is the optimal quantum efficiency of Photosystem II, defined as (Fmax-Fo)/Fmax. This can be a quick method of determining if the algae have been exposed to harmful agents.

EXAMPLE II

Figure 2:
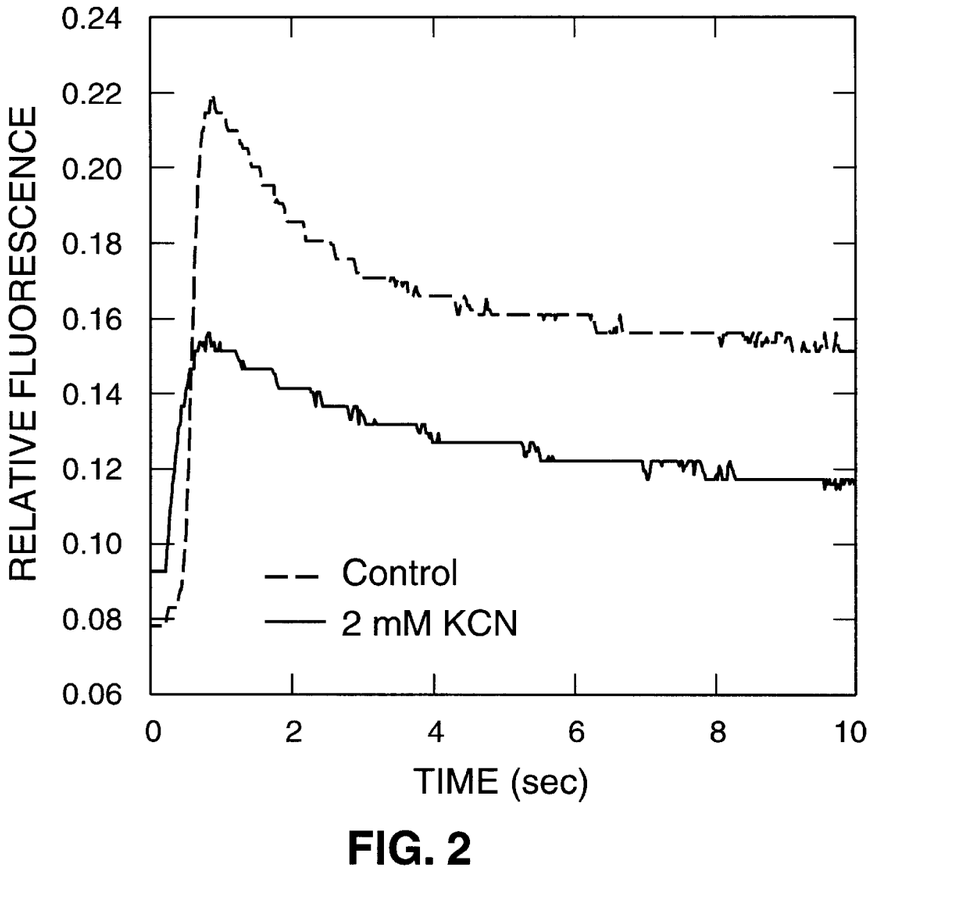
FIG. 2. is a graph illustrating fluorescence induction curves in Clinch river plankton before and after treatment with KCN.

FIG. 2 is an illustration of the detection of potassium cyanide (KCN), a well known poison. The experimental protocol was similar to that of Example I above. Control and sample fluorescence curves are illustrated. Six minutes after exposure of the sample to a 2 mM final concentration of KCN, a clear difference between control and sample can be observed, including a widening of the maximal fluorescence peak (P) in the KCN curve that indicates slower fluorescence quenching after maximal fluorescence has been reached. The $F_o$ and $F_{max}$ values are altered as well. This fluorometric sensing technique can detect cyanide at concentrations below the minimum level for human toxicity.

EXAMPLE III

Figure 3:
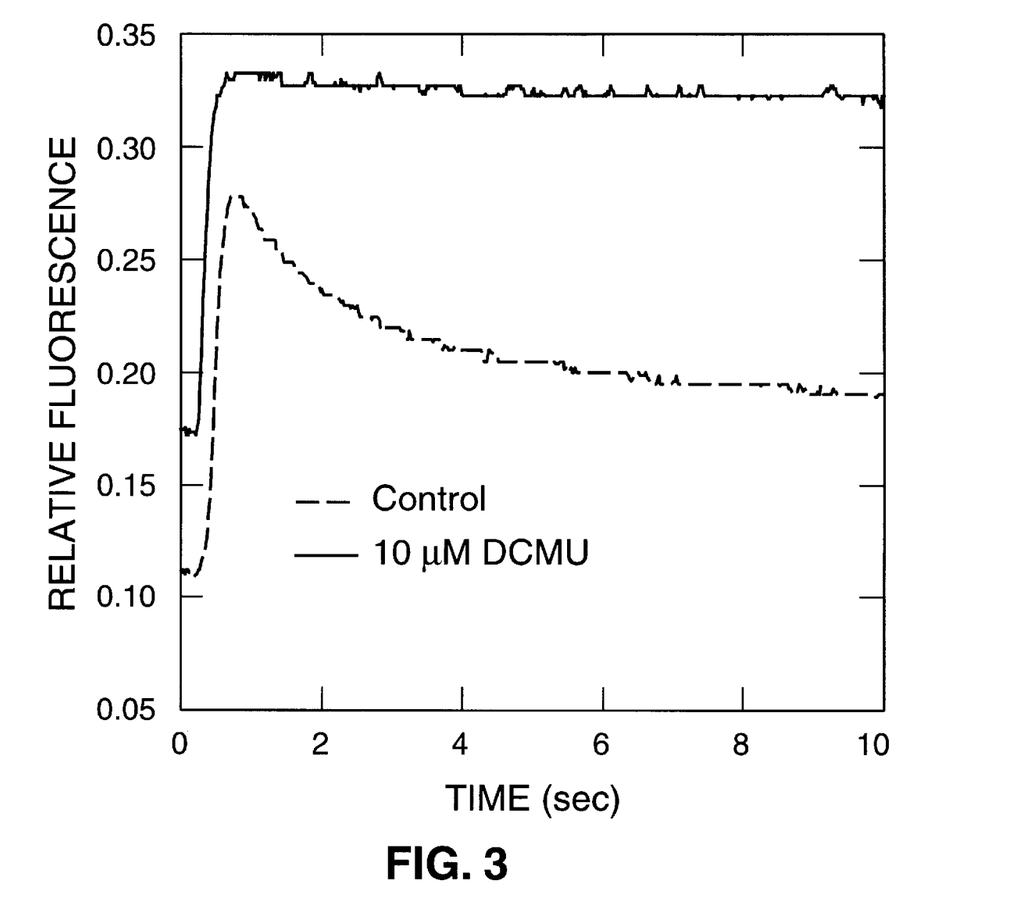
FIG. 3. is a graph illustrating fluorescence induction curves from Clinch river plankton treated with DCMU.

The effect of herbicide 3-(3,4-dichlorophenyl)-1,1-dimethylurea (DCMU) on the water sample fluorescence induction curve was tested in a manner similar to Example I above. When DCMU was added to the cuvette, fluorescence increased considerably and was accompanied by a dramatic change in kinetic time course. A test fluorescence curve (FIG. 3) was recorded after a 6-minute exposure using a final concentration of 10 $\mu$M DCU.

Figure 4:
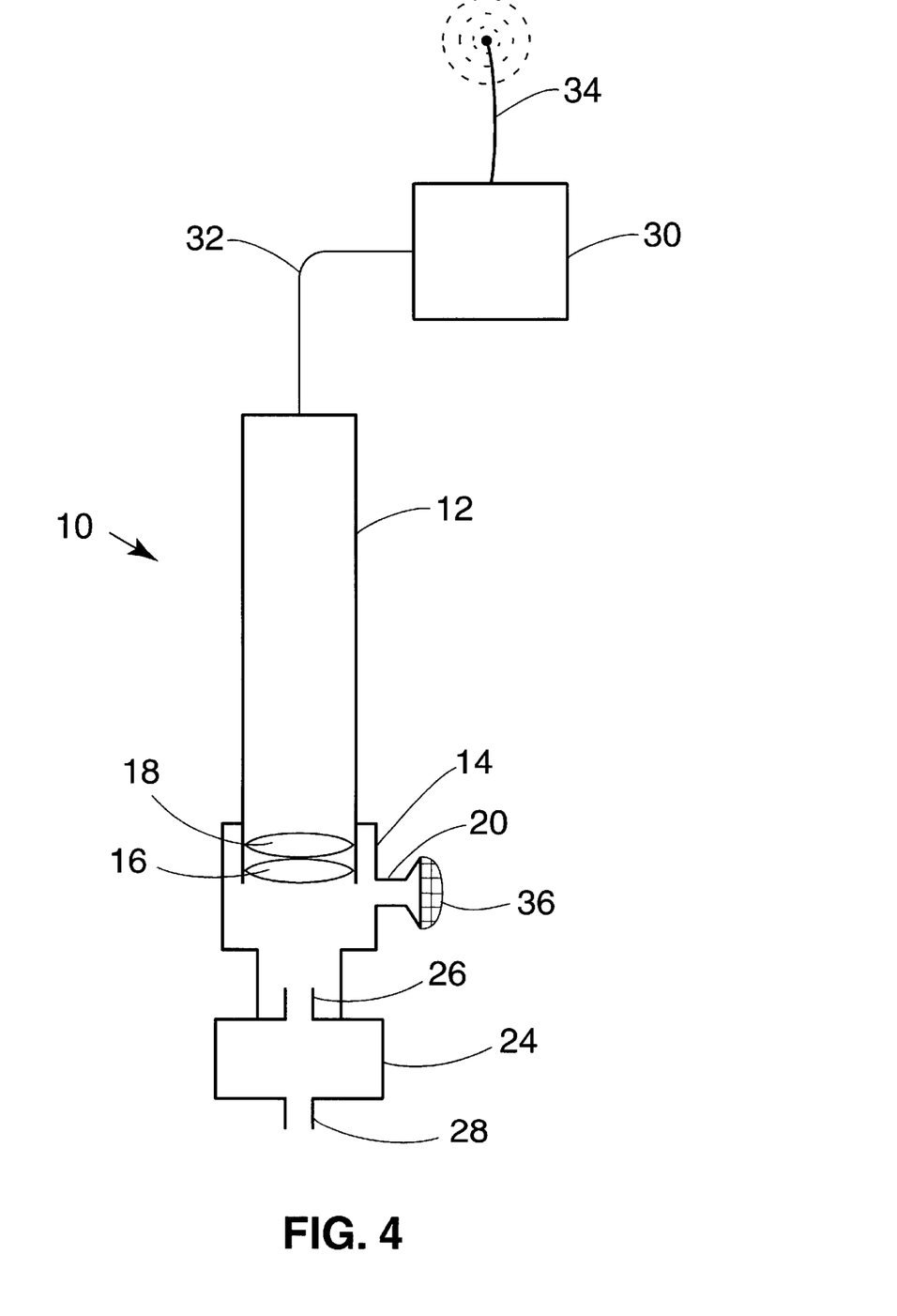
FIG. 4 is an illustration of a basic indigenous-photosynthetic-tissue-based biosensor in accordance with an embodiment of the present invention.

A simple biosensor 10 for carrying out the method of present invention is shown schematically in FIG. 4. A fluorometer 12 is attached to a cell 14 so that a cell window 16 faces the fluorometer input 18. The cell has an inlet 20 having an optional particulate filter 36 and an outlet 26 for passing water therethrough. A pump 24 draws water from the outlet 26 and expels same through an exit 28. The cell 14 could have a displacement pump which draws water into the cell and expels same through a common inlet/outlet opening (analogous to 20), obviating outlet 26 and exit 28. Any means for introducing water into the cell and discharging water from the cell is suitable for carrying out the present invention.

The fluorometer 12 must be of sufficient sensitivity for measuring photosynthetic activity of naturally occurring, free-living, indigenous photosynthetic organisms drawn into the cell 14 with sample water. Applicants used a Walz XE-PAM pulse-amplitude-modulation fluorometer available from Heinz Walz GmbH•Eichenring 6•D-91090 Effeltrich•GERMANY Phone: +49-(0)9133/7765-0•Telefax: +49-(0)9133/5395•E-Mail: info@mail.walz.com. The Walz XE-PAM fluorometer is described in detail at the following Internet web site: http://www.walz.com/pamzta.htm.

The fluorometer is electrically connected by a connector 32 to an electronics package 30, which includes a power supply, systems for operating the fluorometer 12 and pump 24, data processing electronics, and a transmitter that transmits a signal through an antenna 34. The electronics package 30 contains commonly used devices that are well known in the art. The particular components that are used therein, and the particular method of gathering, processing, and transmitting data are not critical to the operation of the present invention.

Operation of the biosensor 10 can be constant sampling or intermittent sampling. Intermittent operation can be random sampling or timed sampling. The pump 24 is operated to cause water to flow through the cell 14. The fluorometer 12 is activated to measure fluorescence in the water flowing through the cell 14. The electronics package 30 analyzes raw data from the fluorometer 12, and emits a signal through the antenna 34 indicating the presence and/or absence of chemical warfare agent(s) in the water. The signal is received by equipment that indicates and/or records the data.

Figure 5:
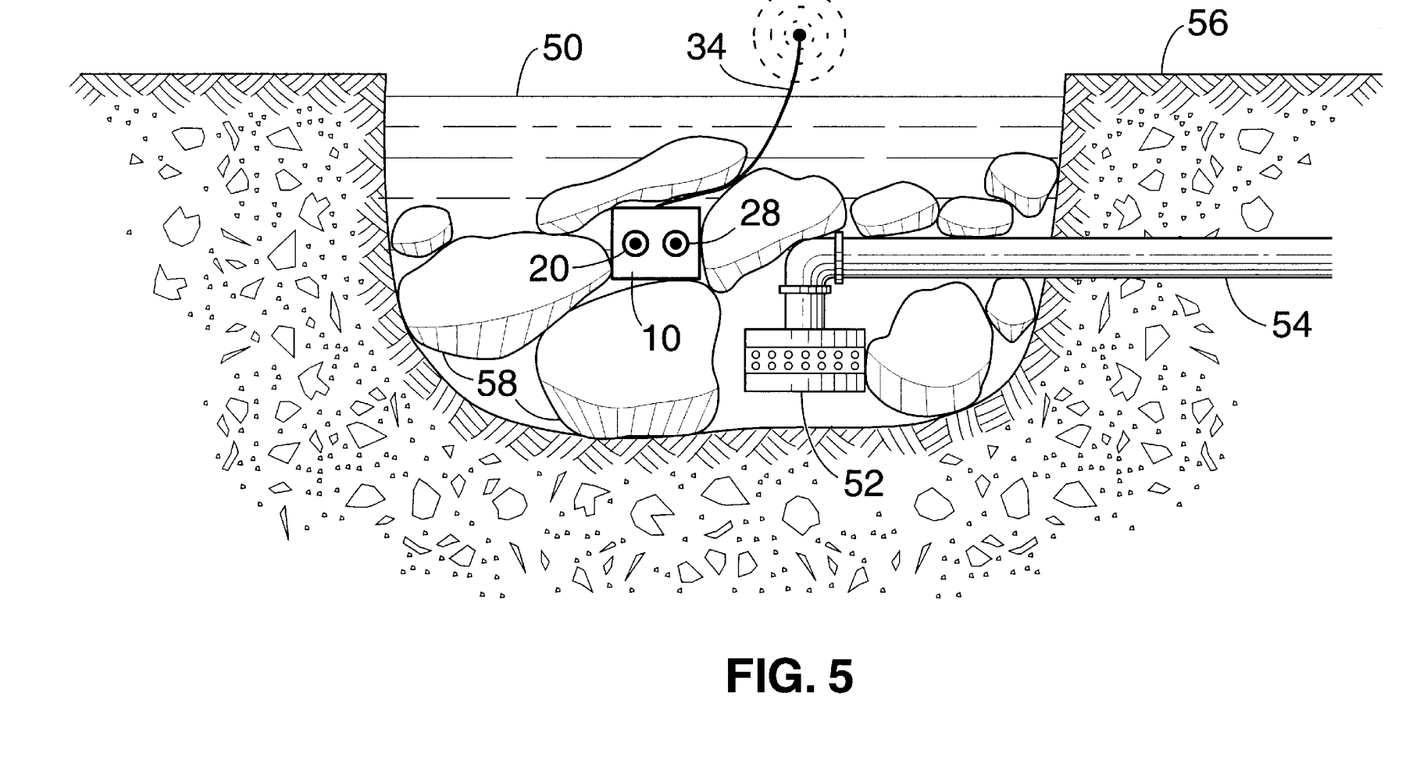
FIG. 5 is an illustration of a sentinel-type biosensor in accordance with an embodiment of the present invention.

In a stationary embodiment of the invention, the biosensor is a sentinel, as shown schematically in FIG. 5 in a typical water supply. A stream 50 is shown cross-sectionally in FIG. 5 as a water source. The water source can be a creek, river, canal, lake, pond, spring, or any other source of water that contains photosynthetic microorganisms. A submerged water intake strainer 52 and intake pipe 54 are shown. The pipe 54 is buried under the ground 56 to hide it from enemies. Rocks 58 in the stream 50 are used to hide the intake 52. Also hidden in the rocks 58 (or even disguised as a rock, plant, or etc.) at or upstream from the intake 52 is a biosensor 10 with its antenna 34. The biosensor 10 will detect and report chemical and/or biological warfare agents that have been used to contaminate the water and injure personnel that drink the water.

Figure 6:
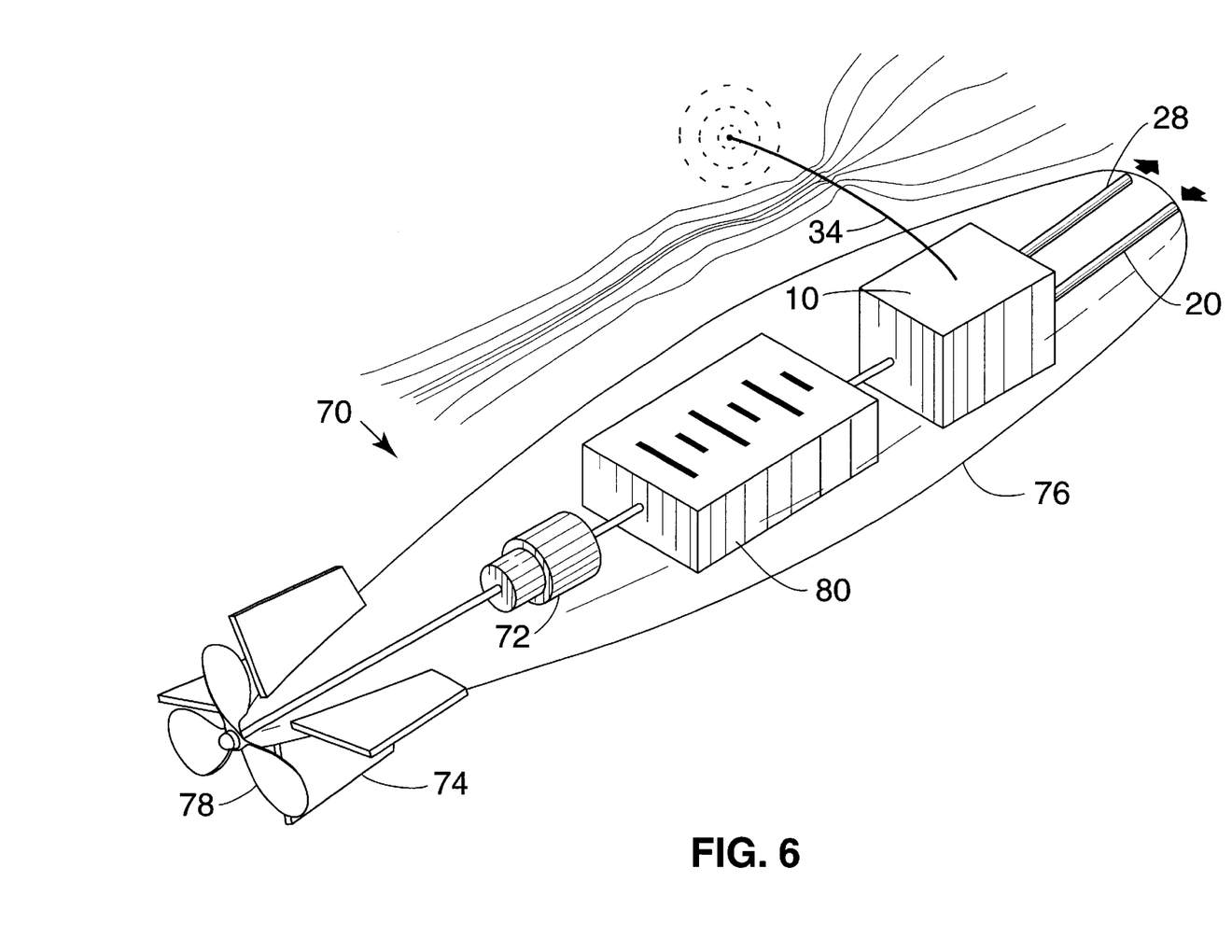
FIG. 6 is an illustration of a submarine-type biosensor in accordance with an embodiment of the present invention.

In a mobile embodiment of the invention, the biosensor 10 is installed inside a miniature water-going vessel such as a boat or preferably a submarine 70, as shown schematically in FIG. 6, which is suitable for placement of a biosensor in a large water supply source such as a lake, wide river, or large pond. The submarine 70 typically has a hull 76, control surfaces 74, a propeller 78, a submarine propulsion and control system 72, and a power supply 80. The power supply 80 supplies power to the propulsion and control system 72 and optionally to the biosensor 10. The submarine 70 is programmed to move about in a body of water, sample the water, and detect and report chemical and/or biological warfare agents that have been used to contaminate the water and injure personnel which drink the water.

The present invention confers practical advantages that are not heretofore known or appreciated. These include: no problems with sensor fouling and therefore no need to replace the sensor; continuous read-out; and long-term stability of the system.

While there has been shown and described what are at present considered the preferred embodiments of the invention, it will be obvious to those skilled in the art that various changes and modifications can be prepared therein without departing from the scope of the inventions defined by the appended claims.

What is claimed is:

1. A water quality sensor for detecting the presence of at least one chemical or biological warfare agent comprising: a cell adapted for analyzing photosynthetic activity of naturally occurring, free-living, indigenous photosynthetic organisms in water; means for introducing water into said cell and discharging water from said cell; a fluorometer for measuring photosynthetic activity of naturally occurring, free-living, indigenous photosynthetic organisms drawn into said cell; and an electronics package that analyzes raw data from said fluorometer and emits a signal indicating the presence of at least one chemical or biological warfare agent in said water.

2. The sensor in accordance with claim 1 wherein said moving means further comprises a submarine.

* * * * *